US011625828B2

(12) United States Patent
Parrish et al.

(10) Patent No.: US 11,625,828 B2
(45) Date of Patent: Apr. 11, 2023

(54) COST EFFECTIVE, MASS PRODUCIBLE SYSTEM FOR RAPID DETECTION OF FEVER CONDITIONS BASED ON THERMAL IMAGING

(71) Applicant: Seek Thermal, Inc., Goleta, CA (US)

(72) Inventors: William J. Parrish, Santa Barbara, CA (US); Jacob Collins, Santa Barbara, CA (US); Ross E. Williams, Santa Barbara, CA (US)

(73) Assignee: Seek Thermal, Inc., Goleta, CA (US)

( * ) Notice: Subject to any disclaimer, the term of this patent is extended or adjusted under 35 U.S.C. 154(b) by 66 days.

(21) Appl. No.: 17/202,976

(22) Filed: Mar. 16, 2021

(65) Prior Publication Data

US 2021/0295517 A1  Sep. 23, 2021

Related U.S. Application Data

(60) Provisional application No. 63/045,616, filed on Jun. 29, 2020, provisional application No. 63/011,692, (Continued)

(51) Int. Cl.
*G06T 7/00* (2017.01)
*G06T 7/80* (2017.01)
(Continued)

(52) U.S. Cl.
CPC .......... *G06T 7/0014* (2013.01); *A61B 5/0077* (2013.01); *A61B 5/015* (2013.01);
(Continued)

(58) Field of Classification Search
CPC .................... G06T 7/0014; G06T 7/80; G06T 2207/30088; G06T 2207/30201;
(Continued)

(56) References Cited

U.S. PATENT DOCUMENTS

2007/0153871 A1\* 7/2007 Fraden .................. A61B 5/015
374/121

FOREIGN PATENT DOCUMENTS

CN     207 515 910 U    6/2018
EP     1 646 310 A2     4/2006
(Continued)

OTHER PUBLICATIONS

"Using Circuit Board Materials for Thermal Control in Medical Diagnostics" Keytech, Jun. 1, 2015, vol. 2016/06.

*Primary Examiner* — Tat C Chio
(74) *Attorney, Agent, or Firm* — Knobbe Martens Olson & Bear LLP

(57) ABSTRACT

Systems and methods based on thermal imaging for rapid detection of fever conditions in humans that provide for extremely inexpensive, mass producible, field deployable devices accurate in specific, relatively low temperature ranges, and in particular temperatures near nominal human body temperature. The system may include a thermal imager tailored for the application and a corresponding mass producible controlled temperature calibration source configured to provide real time calibration near the human body temperature of interest. The imager and source are deployed in a way such that target people and the calibration source will be within the imager FOV for fever detection. The combination of real time near measurement temperature calibration, with suitable thermography approaches, yield fast, accurate measurements in the fever range using low cost, easy-to-produce components. In combination with a visible imager and pattern/facial recognition techniques, detection of a human target's facial regions of interest suitable for fever detection can be accurately accomplished.

26 Claims, 12 Drawing Sheets

Related U.S. Application Data filed on Apr. 17, 2020, provisional application No. 63/003,754, filed on Apr. 1, 2020, provisional application No. 62/990,971, filed on Mar. 17, 2020.

(51) Int. Cl.
| | | |
|---|---|---|
| *A61B 5/00* | (2006.01) | |
| *A61B 5/01* | (2006.01) | |
| *G01J 5/10* | (2006.01) | |
| *H04N 5/232* | (2006.01) | |
| *H04N 5/247* | (2006.01) | |
| *G06V 10/143* | (2022.01) | |
| *G06V 40/16* | (2022.01) | |
| *G01J 5/00* | (2022.01) | |

(52) U.S. Cl.
CPC ............ *A61B 5/7246* (2013.01); *A61B 5/742* (2013.01); *A61B 5/7405* (2013.01); *G01J 5/10* (2013.01); *G06T 7/80* (2017.01); *G06V 10/143* (2022.01); *G06V 40/166* (2022.01); *H04N 5/23229* (2013.01); *H04N 5/247* (2013.01); *A61B 2560/0238* (2013.01); *G01J 2005/0077* (2013.01); *G06T 2207/30088* (2013.01); *G06T 2207/30201* (2013.01)

(58) Field of Classification Search
CPC ..... A61B 5/0077; A61B 5/015; A61B 5/7246; A61B 5/7405; A61B 5/742; A61B 2560/0238; G01J 5/10; G01J 2005/0077; G06V 10/143; G06V 40/166; H04N 5/23229; H04N 5/247
See application file for complete search history.

(56) References Cited

FOREIGN PATENT DOCUMENTS

| EP | 2 793 006 A2 | 10/2014 | |
|---|---|---|---|
| JP | S61 76925 | 4/1986 | |
| KR | 2017050936 A | * 5/2017 | ........... A61B 5/0077 |
| WO | WO 2005/027578 A1 | 3/2005 | |
| WO | WO 2018/194658 A1 | 10/2018 | |

\* cited by examiner

COST EFFECTIVE, MASS PRODUCIBLE SYSTEM FOR RAPID DETECTION OF FEVER CONDITIONS BASED ON THERMAL IMAGING

INCORPORATION BY REFERENCE

This application claims the benefit of U.S. Provisional Application Ser. No. 62/990,971, filed Mar. 17, 2020; U.S. Provisional Application Ser. No. 63/003,754, filed Apr. 1, 2020; U.S. Provisional Application Ser. No. 63/011,692, filed Apr. 17, 2020; and U.S. Provisional Application Ser. No. 63/045,616, filed Jun. 29, 2020, each of which is incorporated herein by reference in its entirety. The following applications are also incorporated herein by reference in their entirety: U.S. application Ser. No. 16/809,387, filed Mar. 4, 2020; U.S. Provisional Application Ser. No. 62/990,997, filed Mar. 17, 2020; U.S. Provisional Application Ser. No. 63/003,730, filed Apr. 1, 2020; and U.S. Provisional Application Ser. No. 63/026,612, filed May 18, 2020.

FIELD

The present disclosure generally relates to imaging systems including thermal imaging sensors, and in particular to a field deployable, inexpensive system for rapid detection of fever conditions.

BACKGROUND

The increasing availability of high-performance, low-cost uncooled thermal imaging devices, such as those based on bolometer focal plane arrays (FPAs), is enabling the design and production of mass produced thermal imaging cameras. Widespread Medical Screening processes involving quick and accurate determination of body temperature lend themselves to thermal imaging. Unlike most thermal imaging processes, some medical applications need be accurate only over narrow temperature ranges, making it possible to produce large numbers of inexpensive thermal imagers suitable for those applications.

SUMMARY

The systems of this disclosure each have several innovative aspects, no single one of which is solely responsible for its desirable attributes. Without limiting the scope as expressed by the claims that follow, its more prominent features will now be discussed briefly.

Systems and methods based on thermal imaging for rapid detection of body temperature which may be related to fever conditions in humans may be provided that produce inexpensive, mass producible, field deployable devices accurate in specific, relatively low temperature ranges, and in particular temperatures near nominal human body temperature. The system may include a thermal imager tailored for the application and a corresponding mass producible controlled temperature calibration source configured to provide real time calibration near the human body temperature of interest. The imager and source are deployed in a way such that target people and the calibration source will be within the imager field of view (FOV) for fever detection. The combination of real-time near-measurement temperature calibration, with suitable thermography approaches, yield fast, accurate measurements in the fever range using low cost, easy-to-produce components. In combination with a visible imager and pattern/facial recognition techniques, detection of a human target's facial regions of interest suitable for fever detection can be accurately accomplished.

In a first aspect, a system for measuring the temperature of a region of interest of a target is described. The system includes at least one system controller; at least one visible camera interfaced to the controller; at least one thermal camera interfaced to the controller, wherein at least a portion of image pixel locations from the visible and thermal cameras are mapped to each other, and wherein the thermal camera has a thermography function based on a previous pixel-by-pixel calibration of at least some pixels of the thermal camera; and at least one temperature controlled calibration source of a known shape. When the target and the calibration source are within a field of view (FOV) of both cameras, the system controller is configured to obtain a visible image using the at least one visible camera and a thermal image using the at least one thermal camera; locate the calibration source in the thermal image by performing pattern recognition on at least one of the visible image and the thermal image; perform a temperature calibration of a subset of pixels in the thermal image, the subset of pixels corresponding to the calibration source; update a thermography function of the thermal camera based on a known temperature of the calibration source; detect, using pattern recognition, visible region of interest pixels in the visible image and thermal region of interest pixels in the thermal image; refine the thermal region of interest pixels based on the pattern recognition; and perform an updated thermography readout of the refined thermal region of interest pixels to produce a real-time calibrated temperature measurement based on the thermal region of interest pixels.

In some embodiments, the target comprises an upper body region of a human, and the region of interest comprises a portion of a facial region of the target.

In some embodiments, the known temperature of the calibration source is at least one of within 15 degrees, within 10 degrees or within 5 degrees of a nominal human body temperature. In some embodiments, the temperature measurement is within a range corresponding to within at least one of 15, 10, or 5 degrees above nominal human body temperature. In some embodiments, the temperature measurement is a threshold measurement indicative of the target having a fever. In some embodiments, the region of interest pixel detection and mapping, the calibration source location, and the temperature calibration are updated periodically after a number of frames. In some embodiments, the number of frames is one, and the update is on a frame-by-frame basis. In some embodiments, the threshold temperature measurement is based on a highest temperature pixel of the thermal region of interest pixels, statistically derived over the number of frames. In some embodiments, the number of frames is 8 and the statistical derivation is a boxcar average of the highest temperature pixel of the thermal region of interest pixels in each of the 8 frames. In some embodiments, the threshold temperature measurement is based on a statistical derivation of a number of the highest temperature pixels in the region. In some embodiments, the threshold temperature measurement of each frame is further statistically derived over a number of frames.

In some embodiments, the system further includes a user interface interfaced to the system controller, the user interface comprising at least one of audio or visible indicators of measurement validity based on verified detection of the target and the calibration source.

In some embodiments, the system further comprises at least one of audio or visible indicators of a target temperature above a threshold.

In some embodiments, locating the calibration source in the thermal image comprises at least one of identifying pixels of the known shape of the calibration source in the thermal image, or recognizing at least one of the source shape or color in the visible image and mapping to the corresponding thermal pixels.

In some embodiments, the source location is further derived by recognizing at least one of the source shape or color in the visible image and supplementing the data from the thermal image.

In some embodiments, pixels in a mapped facial region within a predetermined temperature range of the calibration source temperature are identified, and facial region coordinates in the thermal image are updated based on the identified pixels.

In some embodiments, an actual size of at least one of the calibration source and a facial region are compared to the known size at a nominal distance from the cameras, and an estimate of actual distance based on the comparison is used to adjust the thermography function for distance.

In some embodiments, the system controller is further configured to use a nominal target temperature for a first target; acquire and store actual measured skin temperatures for a number of successive targets; keep a running statistical value, including at least one of an average, median, or other statistical value, of actual skin temperatures of the successive targets; obtain a sufficient number of data points, including at least one of a predetermined threshold number of data points or a sufficient number wherein deviations from the statistical value fall within a predetermined range; and substitute the running statistical value for the nominal target temperature for at least some subsequent temperature measurements. In some embodiments, outliers are eliminated, and a statistical value of remaining center temperatures are used as the nominal target temperature. In some embodiments, the nominal target temperature is periodically updated after at least one of every successive target after the initial number or after a predetermined number of targets.

In a second aspect, a method is described for measuring the temperature of a region of interest of a target with a system comprising at least one visible camera and at least one thermal camera interfaced to a system controller, wherein at least a portion of image pixel locations from the visible and thermal cameras are mapped to each other, and wherein the thermal camera has a thermography function based on a previous pixel-by-pixel calibration of at least some pixels of the thermal camera, the system further comprising at least one temperature controlled calibration source of a known shape. The method comprises causing the target and the calibration source to be within a field of view (FOV) of both cameras; obtaining a visible image using the at least one visible camera and a thermal image using the at least one thermal camera; locating the calibration source in the thermal image by performing pattern recognition on at least one of the visible image and the thermal image; performing a temperature calibration of a subset of pixels in the thermal image, the subset of pixels corresponding to the calibration source; updating a thermography function of the thermal camera based on a known temperature of the calibration source; detecting, using pattern recognition, visible region of interest pixels in the visible image and thermal region of interest pixels in the thermal image; refining the thermal region of interest pixels based on the pattern recognition; and performing an updated thermography readout of the refined thermal region of interest pixels to produce a real-time calibrated temperature measurement based on the thermal region of interest pixels.

In some embodiments, the target comprises an upper body region of a human, and the region of interest comprises a portion of a facial region of the target.

In some embodiments, the known temperature of the calibration source is at least one of within 15 degrees, within 10 degrees or within 5 degrees of a nominal human body temperature. In some embodiments, the temperature measurement is within a range corresponding to within at least one 15, 10, or 5 degrees above nominal human body temperature. In some embodiments, the temperature measurement is a threshold measurement indicative of the target having a fever. In some embodiments, the region of interest pixel detection and mapping, the calibration source location, and the temperature calibration are updated periodically after a number of frames. In some embodiments, the number of frames is one, and the update is on a frame-by-frame basis. In some embodiments, the threshold temperature measurement is based on a highest temperature pixel of the thermal region of interest pixels, statistically derived over the number of frames. In some embodiments, the number of frames is 8 and the statistical derivation is a boxcar average of the highest temperature pixel of the thermal region of interest pixels in each of the 8 frames. In some embodiments, the threshold temperature measurement is based on a statistical derivation of a number of the highest temperature pixels in the region. In some embodiments, the threshold temperature measurement of each frame is further statistically derived over a number of frames.

In some embodiments, the system includes a user interface interfaced to the system controller, the user interface comprising at least one of audio or visible indicators of measurement validity based on verified detection of the target and the calibration source.

In some embodiments, the system includes a user interface interfaced to the controller, comprising at least one of audio or visible indicators of over threshold target temperature.

In some embodiments, the source location is further derived by recognizing at least one of the source shape or color in the visible image and supplementing the data from the thermal image.

In some embodiments, the pixels in the mapped facial region within a predetermined temperature range of the source temperature are identified, and the facial region coordinates in the thermal image are updated based on the temperature identified pixels.

In some embodiments, an actual size of at least one of the calibration source and a facial region are compared to a known size at a nominal distance from the cameras, and an estimate of actual distance based on the comparison is used to adjust the thermography function for distance.

In some embodiments, the method further comprises using a nominal target temperature for a first target; acquiring and storing actual measured skin temperatures for a number of successive targets; keeping a running statistical value, including at least one of an average, median, or other statistical value, of actual skin temperatures of the successive targets; obtaining a sufficient number of data points, including at least one of a predetermined threshold number of data points or a sufficient number wherein deviations from the statistical value fall within a predetermined range; and substituting the running statistical value for the nominal target temperature for at least some subsequent temperature measurements. In some embodiments, outliers are eliminated, and a statistical value of remaining center temperatures are used as the nominal target temperature. In some embodiments, the nominal target temperature is periodically updated after at least one of every successive target after the initial number or after a predetermined number of targets.

BRIEF DESCRIPTION OF THE DRAWINGS

The above-mentioned aspects, as well as other features, aspects, and advantages of the present technology will now be described in connection with various implementations, with reference to the accompanying drawings. The illustrated implementations are merely examples and are not intended to be limiting. Throughout the drawings, similar symbols typically identify similar components, unless context dictates otherwise.

DETAILED DESCRIPTION

Figure 1:
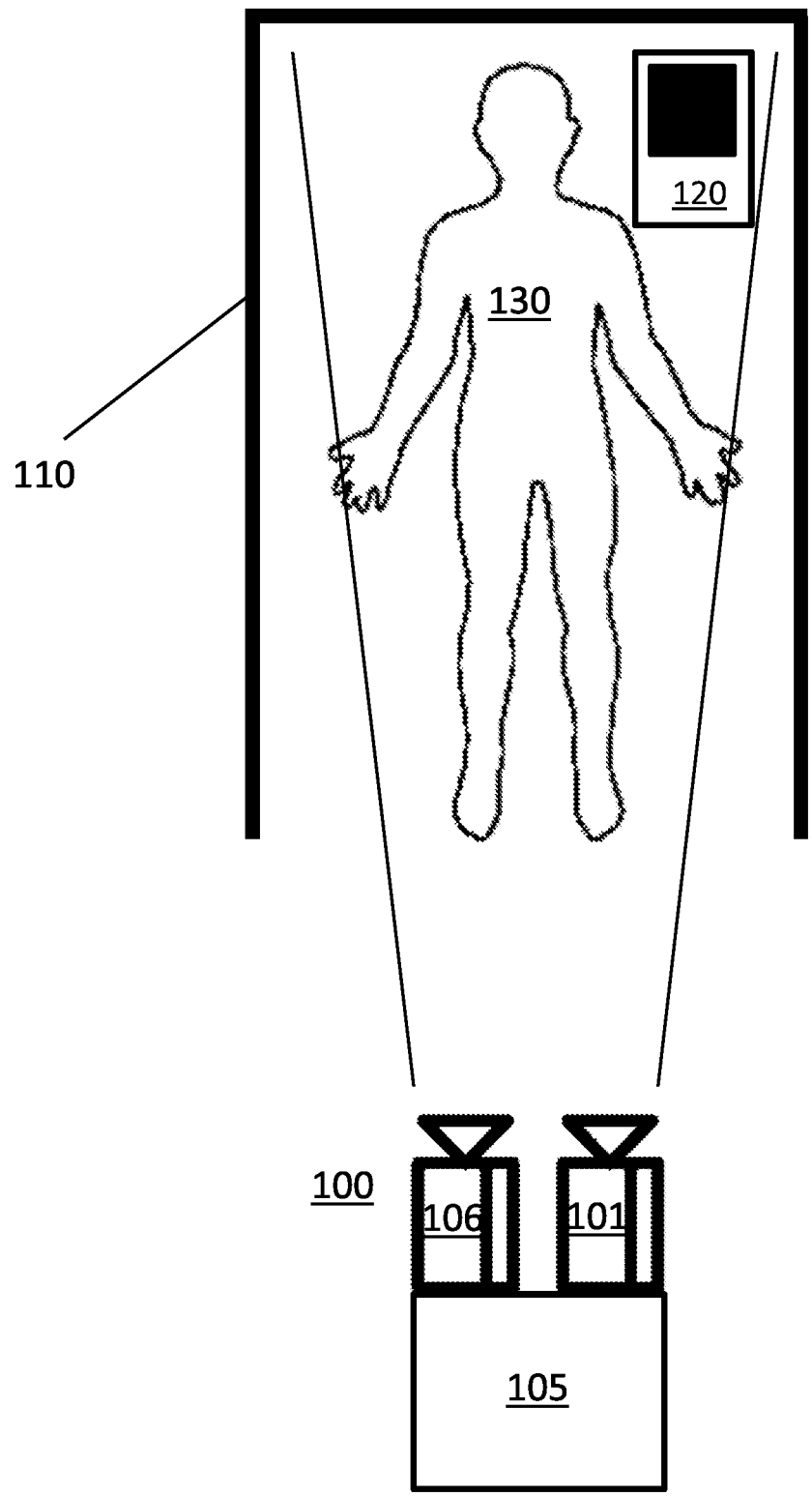
FIG. 1 schematically illustrates an exemplary arrangement of a thermal imaging system in use in accordance with the present technology.

The following description is directed to certain implementations for the purpose of describing the innovative aspects of this disclosure. However, a person having ordinary skill in the art will readily recognize that the teachings herein can be applied in a multitude of different ways.

Generally described, embodiments of the present disclosure relate to applying thermal imaging to applications where the performance requirements are reduced compared to general purpose thermal imaging. For such applications it may be possible to provide thermal imaging components that are very inexpensive and can be produced and deployed in large quantities, while still maintaining adequate performance for the particular application.

A particular application suitable for thermal imaging of great current interest is the rapid detection of fever conditions in human beings, particularly with regards to workplaces, travel, entertainment and sports venues, restaurants, hospitality providers, and other situations where it is desirable to prevent people that are sick from close interaction with numbers of others, for example, any group setting in which multiple people from different households or locations may gather in close proximity and/or within an enclosed space. This application is rapidly growing with the advent of new epidemic and pandemic type illnesses whose spread is critical to control by avoiding person-to-person transmission in group settings.

Fever detection applications in accordance with the present technology may be based on the measurement of a skin temperature at the surface of the body, which is related to internal body temperature. In some aspects, fever detection may be especially suitable for thermal imaging, as compared to many other thermal image applications that must perform over a wide range of scene temperatures. The temperature range of interest is relatively small, basically within a few degrees of a nominal body temperature (e.g., within a span of approximately 10 degrees C. or less). Because human body temperature is typically higher than most ambient temperatures, these relevant temperatures may appear as high-contrast ranges compared to most ambient temperatures in the locations where such systems are implemented. Additionally, the spatial resolution requirements of such imaging systems may be satisfied, for example, as long as portions of a face can be resolved within the field of view (FOV) of a thermal camera, usually achievable assuming the imaging is done as people pass through doorways, check points or other controlled access arrangements where the distance from the imager to the target can be suitably controlled.

Thus, accurate temperature measurements within specifically defined narrow temperature ranges may be suitable. Thermal cameras suitable for such applications may allow for significantly less stringent specifications and manufacturing tolerances than high performance general purpose thermal cameras.

One aspect that remains challenging, however, is that even for the defined temperature range of interest (e.g., a range of 10 degrees C. or less), the accuracy of thermography (e.g., determination of surface or scene temperature based on the signal output of an imager such as a focal plane array) over that relatively small range needs to be very accurate. For example, in various implementations, desired resolution within the temperature range of interest may be 2 degrees C., 1 degree C., 0.5 degrees C., 0.25 degrees C., or better. Achieving such accuracy over time and varying ambient temperature is difficult for low cost thermal imaging devices and systems.

A novel approach, as disclosed in accordance with the present technology, is to accept that the thermal imagers, in order to be accessible from a cost and availability standpoint, may not be able to provide the desired performance alone. A solution may be to perform a real-time thermography calibration in the field at or within the temperature range of interest, using cost-effective components suitable for this particular task. As will be discussed in greater detail herein, even a lower-performance thermal imaging device may be adapted to perform very precisely within a desired range (e.g., within a few degrees, up to 10 degrees C. or more) of a calibration temperature, by calibrating the thermal imaging device repeatedly (e.g., periodically, occasionally, or continuously) at a given calibration temperature. This field calibration approach is promising. However, to practically implement this approach, a field installable, temperature-controlled calibration source (e.g., a fixed-temperature blackbody or the like) may be desirable. Mass production and widespread deployment of such systems may be improved by the use of calibration sources that can be manufactured with the same cost and manufacturing advantages as the low-cost thermal imagers implemented therewith. Various other innovations, as will be described herein, may further improve the accuracy and reliability of such imaging systems in a mass producible and cost-effective manner.

Referring to FIG. 1, elements of a thermal imaging-based fever detection system are shown. In the specific embodiment of FIG. 1, the target 130 to be analyzed is a human being, although the systems and methods disclosed herein may equally be used with other living or non-living targets. To increase reliability, it may be advantageous to arrange the operation so that the target is either funneled into or directed into a defined space (e.g., space 110) where the target's position is generally constrained, at least for enough time to take the desired temperature measurements. Such times, as will be explained below, may be relatively short, such as on the order of a few seconds or less.

An arrangement such as the configuration of FIG. 1 may take advantage of a constrained condition that already occurs in many cases where fever monitoring is appropriate, such as airport security screening areas or public event spaces (e.g. sports events, concerts, and the like). For example, the constrained space 110 may correspond to an existing space or physical structure such as a walk-through portal (e.g., checkpoints such as the personal item inspections and/or ticket checks common at such locations and events, where metal detectors or other types of walk-through portals are implemented). For smaller gathering venues such as churches, restaurants, stores, and the like, in many cases doorways or entrance hallways may similarly serve to define a target's position momentarily. Alternatively or additionally, defined areas to stand or sit may be used at or near any building entry point. Thus, the condition that a target, advantageously just one target, be in a known position for a short period of time is compatible with many venues where fever screening is desirable. If a naturally occurring or existing constrained location is not present, targets may also be directed into such a space designated specifically for thermal monitoring, analogously to a photo booth arrangement.

Regardless of the physical implementation of the constrained space 110, FIG. 1 illustrates the configuration of a known space 110 in which the position of a target 130 is constrained such that the target 130 at least momentarily stands or sits within the space 110. An imaging unit 100 may contain a thermal camera 106 (e.g., a camera configured for thermal imaging and/or imaging in infrared wavelengths of the electromagnetic spectrum) and a visible camera 101 (e.g., a camera configured for imaging within at least some visible wavelengths of the electromagnetic spectrum). The FOVs of the thermal camera 106 and the visible camera 101 may be at least partially if not completely overlapping. In some embodiments, at least some of the pixels of the thermal camera 106 and at least some of the pixels of the visible camera 101 are mapped or registered to each other to provide for correction of any translational and/or rotational offset of the FOVs of the thermal camera 106 and the visible camera 101. Imaging unit 100 is placed relative to the space 110 such that all or part of target 130 is within the FOV of both cameras when the target 130 is in space 110. Imaging unit 100 may also include one or more support elements 105, for example, a programmable controller of a suitable type and/or other power, monitoring, and/or control components such as a user interface, power supply, and the like.

A temperature-controlled calibration source 120 is positioned in a location within the FOVs of the thermal camera 106 and the visible camera 101. The location of the calibration source 120 may be selected such that the calibration source 120 can be viewed simultaneously (or within a short time frame) with target 130. Various types of controlled calibration sources may be used as calibration source 120, such as but not limited to a type described in co-pending U.S. Provisional Application Ser. No. 63/026,612.

As described above, to achieve the mass producibility and cost-effectiveness needed to make thermal imagers suitable for widespread production and use in this application, trade-offs in performance and stability over time and temperature may need to be made. Such trade-offs can be mitigated if at least a part of the thermal image calibration is updated at or near the time of data acquisition, and the temperature range of interest is narrow around the updated calibration temperature. Thus, the presence of a calibration source (e.g., a blackbody) whose blackbody temperature is at or near (e.g., within 1 degrees C., 10 degrees C., 5 degrees C., or less) of a nominal human body temperature assures that even a low-performance thermal imager will yield suitably accurate temperature data in the range of possible fever temperatures. In some cases, it may be convenient to make the temperature of the calibration source higher than the highest body temperature expected, as the calibration source will then likely be the hottest item in the FOV, and thus particularly easy to identify. In some cases, the calibration source temperature may be in the range of 40 degree C. or higher, for example, in a particular embodiment the calibration source temperature may be chosen to be 42.5 degrees C.

For the embodiment shown, calibration source 120 is simultaneously viewable with target 130, and may be within the FOV of both the thermal camera 106 and the visible camera 101. In some embodiments, the calibration source 120 is at least within the FOV of the thermal camera 106, and may be partially or completely outside of or hidden from the FOV of the visible camera 101. Thus, in the configuration illustrated in FIG. 1, it is possible to perform a temperature calibration on thermal image frames at the same, or nearly the same, time as target data is acquired.

Other arrangements are possible, such as a spatial arrangement in which the target 130 steps in front of the calibration source 120 while passing through the. For this case, the temperature calibration can be performed in between targets entering, thus ensuring that the calibration is near enough in time to still be effective. In another example arrangement, the calibration source 120 may be of a size and/or shape such that a region of interest (e.g., the appropriate part of the target 130 such as a face) may be at least partially in front of the calibration source 120 with the calibration source 120 extending beyond the target dimensions. In some embodiments, this arrangement may provide for desirable accuracy as the measurement may be a direct differential from the known target temperature, with the same pixels calibrated as represent the target region. However, such a large blackbody may be difficult to make inexpensively and power conveniently. Although the following description of the present technology will be described with reference to the arrangement of FIG. 1, it will be understood that these and other arrangements are workable and may be implemented in accordance with the present technology.

Figure 2:
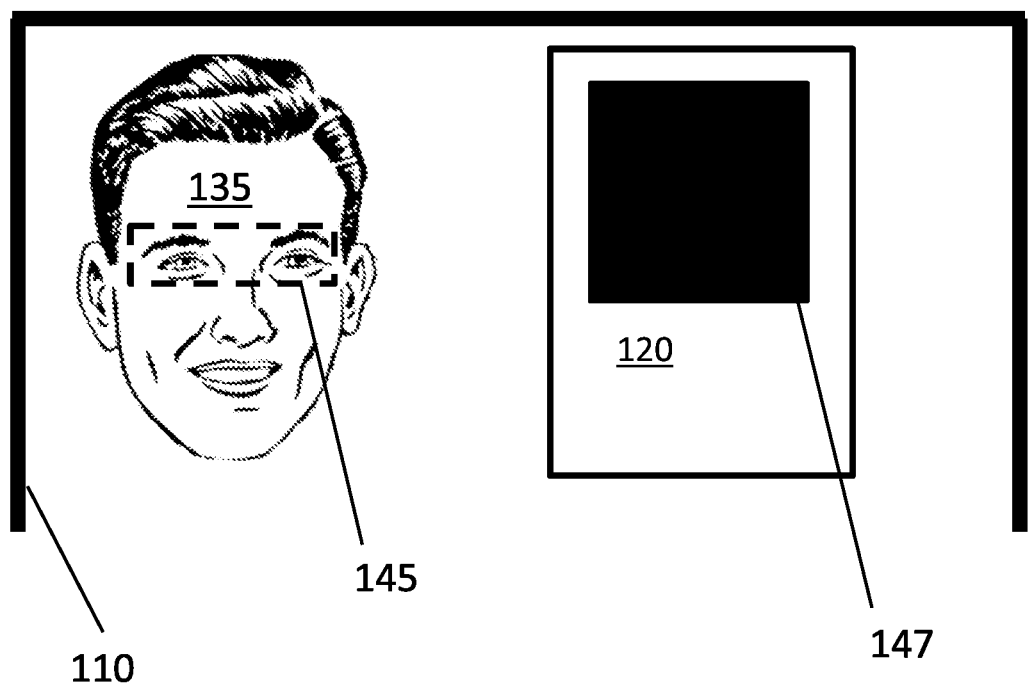
FIG. 2 shows details of the exemplary system of FIG. 1 relative to recognition of regions of interest and a calibration source.

FIG. 2 shows details of specific portions of the FOV within space 110 which may be used to detect fever accurately. The FOV of the cameras 106, 101 does not necessarily need to contain the entire target 130 (FIG. 1), as it is generally sufficient to detect fever based on only the face 135 of a target. However, as targets vary in size and shape, to keep the system simple (e.g., by allowing for a fixed-position imaging unit without requiring any hand-aiming or automatic aiming) it may be desirable to arrange the FOV to capture at least the upper body of all targets of interest. Within the target, the facial region 145 of the face 135 around the nose and eyes is particularly suitable for measuring body temperature.

This facial region 145, as well as an active region 121 of the calibration source 120, can be identified with pattern recognition techniques implemented in conjunction with the thermal camera 106 and the visible camera 101. Using custom or currently available facial recognition software, region 145 may be identified in the visible image. Additionally or alternatively, pattern recognition based on temperature may be applied to the thermal image in conjunction with or separate from the visible image facial recognition. In a further example, the active region 121 of the calibration source 120 may be identified in the thermal image directly, as the shape and temperature may be known. The active region 121 may also be identified or further validated based on the visible image by way of shape. In some embodiments, the calibration source region 121 may be painted or coated with a unique high-contrast color (e.g., red), such that both color and shape can be used to identify the pixels 147 corresponding to the active region 121, which may or may not be a subset of the total region. Further surface treatments, such as textures or fiducials, may similarly be used to aid in recognizing the active region 121 of the calibration source 120.

Figure 3:
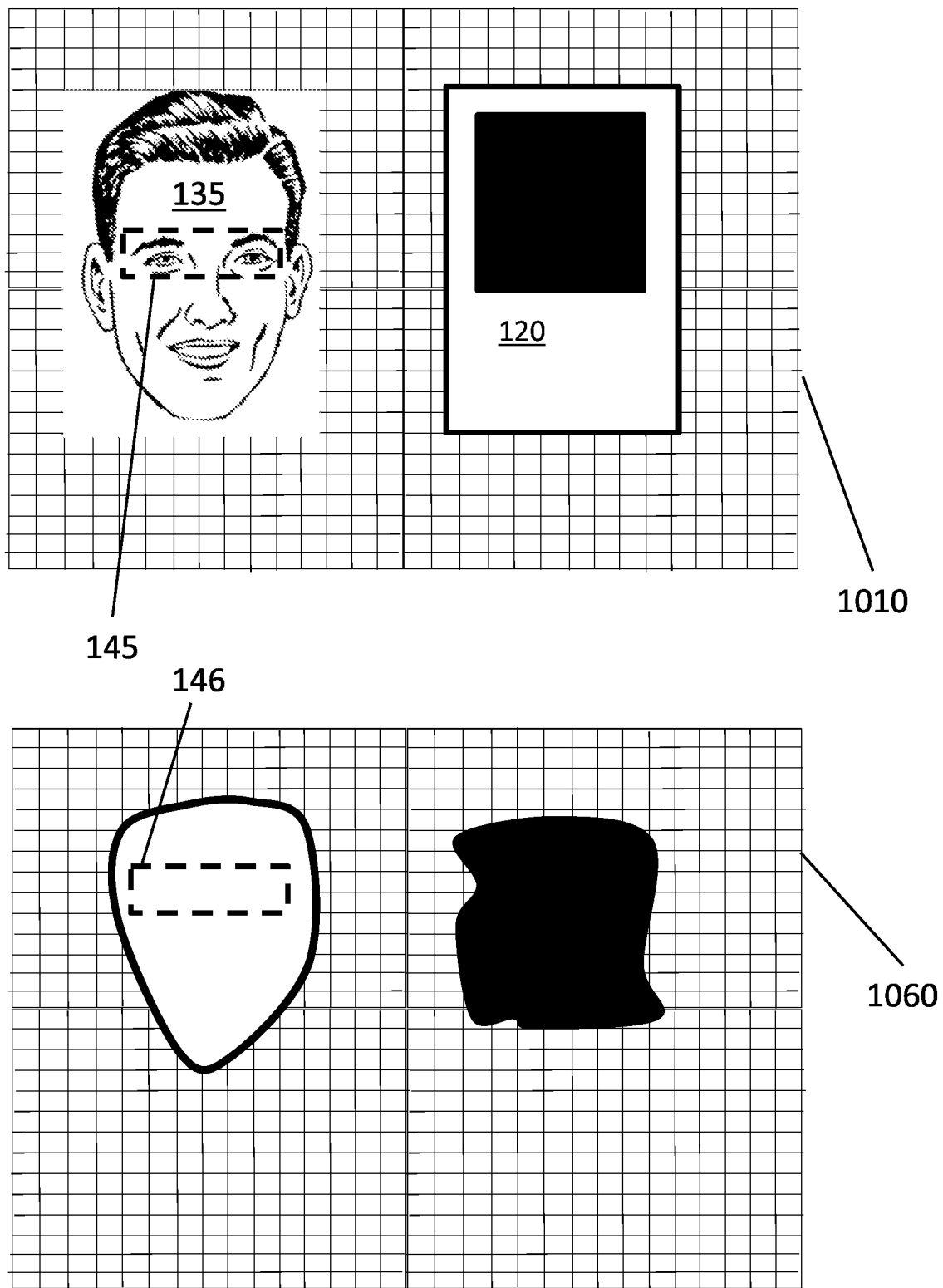
FIG. 3 shows exemplary mapping of regions of interest and the calibration source to thermal image pixels.

FIG. 3 shows an example implementation of the use of pattern recognition in accordance with the present technology. FIG. 3 depicts a visible image frame 1010 captured using the visible camera 101 and a thermal image frame 1060 captured using the thermal camera 106. The visible image frame 1010 is processed with facial/pattern recognition to identify the pixels of interest 145 in the face 135. At or near the same time, pattern recognition is applied to the visible image frame 1010 and the thermal image frame 1060 to identify calibration source pixels of interest, either pixels 147 in the visible image frame 1010 or pixels 148 in the thermal image frame 1060. Target region pixels 145 in the visible image frame 1010 may be mapped or registered to corresponding thermal target region pixels 146 in the thermal image frame 1060. Calibration source region pixels 147 in the visible image frame 1010, or pixels 148 in the thermal image frame 1060, are either mapped from the pattern recognized pixels in the visible image frame 1010 to the corresponding pixels in the thermal image frame 1060, and/or are determined directly from pattern recognition of the thermal image frame 1060. It is often beneficial to combine information from recognition in both thermal and visible images to refine the thermal target region pixels 146. Examples of this process will be described below. At this point, a relatively small number of refined thermal pixels 146 directly suitable for measuring body temperature have thus been identified. Similarly, thermal image pixels 148 corresponding to a known calibration source temperature have further been identified. Pixels 148 can then be used to update the thermal imager thermography calibration as will be explained below.

Figure 4:
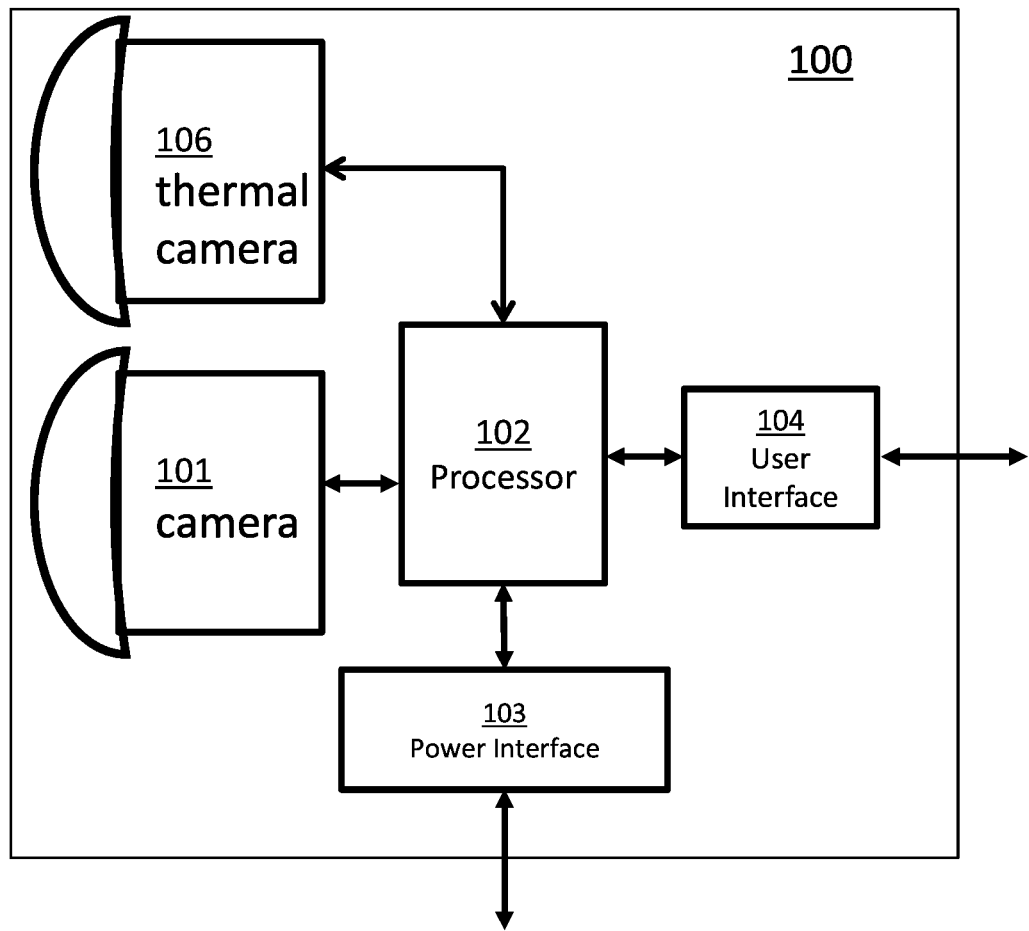
FIG. 4 is a schematic representation of an exemplary imager in accordance with the present technology.

FIG. 4 schematically illustrates components of an imaging unit 100, such as the imaging unit 100 of FIG. 1. Imaging unit 100 may be a two-camera unit, using modern thermal and visible camera cores, easily packaged in a suitably sized housing (e.g., a few inches on a side), and using a relatively small amount of power (e.g., less than 3 watts of power), for example. Thermal camera 106 and visible camera 101 interface to a processor 102 which may be configured to perform operations such as but not limited to acquiring image frames from the visible camera 101 and the thermal camera 106, performing pattern recognition, and performs other function as appropriate. A user interface 104 may be present. The user interface may include a minimal set of indicators and/or may include other components up to and including an application running on an interfaced computing device.

Power interface 103 may include, for example, a USB interface for the imager unit 100, but other power variations are possible. USB is a particularly convenient solution for power, as it is either commonly available in many facilities or can be easily obtained from plug-in USB chargers. Thus, a USB power interface may be relatively simple and inexpensive, along with making unit 100 very easy to install anywhere and providing more than enough power to operate the imaging unit 100. Alternative power interfaces, such as battery, ac-dc converter/battery charger, or a traditional ac power supply would be suitable as well as any other suitable power source. For some installations, direct solar cell power may be implemented as well.

In some embodiments, imaging unit 100 may be interfaced to a network for remote control and data communication. Although not illustrated in FIG. 4, such connections are contemplated in conjunction with the present technology, and the unit 100 may be interfaced to a network without departing from the spirit or scope of the present disclosure.

Figure 5:
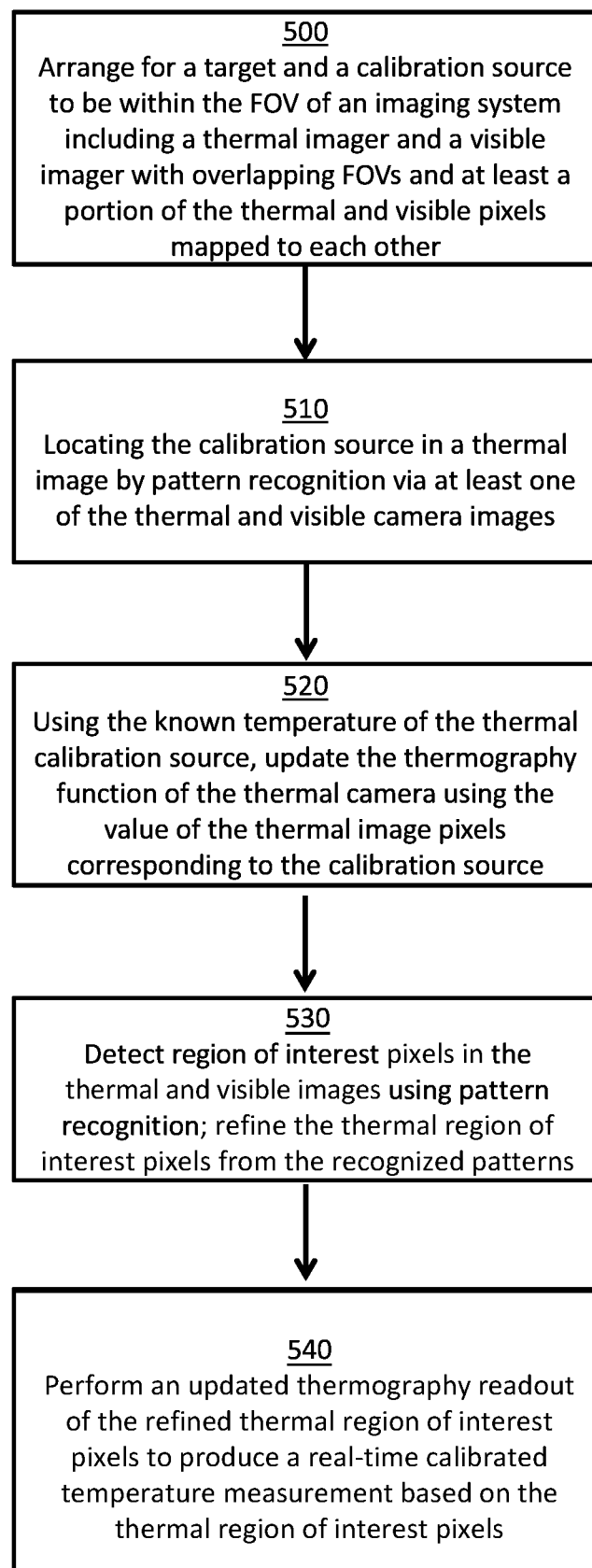
FIG. 5 is a flow chart illustrating an exemplary method of operation of a thermal imaging system in accordance with the present technology.

Turning to FIG. 5, an example method for using the system as described above is shown in flow chart form. In step 500, as discussed above, a target and a calibration source are arranged to be within the FOV of a thermal imager and a visible imager, such as the thermal camera 106 and visible camera 101 of FIGS. 1 and 4. The FOVs of the imagers should at least partially overlap, and the overlapping pixels in the two imagers can be mapped or registered to each other. In general, both the target and the calibration source may be in the overlapping portion of the FOVs. However, it is not strictly necessary that the visible camera see the calibration source, as suitable measures may be obtained if the thermal camera can see both the target and the calibration source.

The calibration source can be in a known fixed location, and therefore the pixels in each thermal image frame corresponding to the source may be predetermined. However, in some embodiments it may be simpler and more robust to find the calibration source in some or all images using pattern recognition, at step 510, dynamically, even as often as every thermal image frame. The image pixels corresponding to the calibration source may be identified directly in the thermal image by pattern recognition using one or both of the shape and temperature of the calibration source, and/or identified in the visible image using one or both of color and shape, and then mapped to the thermal image to identify the thermal pixels corresponding to the pixels of the calibration source in the visible image.

At step 520, the known temperature of the thermal calibration source is used to update a thermography function of the thermal imager. Thermography is a term in thermal imaging that refers to deriving scene temperature from thermal intensity signal. Thermal cameras generally undergo a thermography calibration, often at manufacture, that derives scene temperature for a given pixel from pixel intensity. This can be fairly complex (see, e.g., U.S. application Ser. Nos. 14/838,000, 15/843,667, and 16/809,387, owned by the owner of the current application and incorporated by reference herein). The thermography function may be dependent on both ambient temperature of the imager and pixel intensity. Thus, it may be challenging to produce imagers where this function remains accurate over time, as the thermography relationship may drift over both time and ambient temperature. For the fever application, the thermal imagers need not maintain accurate thermography over a wide range of scene temperature, so rather than go through the expense of producing low drift cameras, it is more efficient and more accurate to simply include a fixed temperature calibration source in the system. The results of the thermography function can be compared to the actual values obtained by viewing the calibration source for the corresponding pixels. From this comparison, performed often, maybe as often as on every frame, modification of the function can be determined for the pixels corresponding to the source and applied to the rest of the thermal pixels. Such modifications are also described in U.S. application Ser. Nos. 14/817,847, 15/068,405, and 16/809,387, and maybe accomplished by an offset to the function. Thus, the thermography function is updated often at the temperature of interest. In some embodiments, two or more calibration temperatures, and/or larger blackbodies that cover more pixels, may be implemented to improve the calibration update, and would possibly eliminate the need for extensive factory calibration as two sources would allow for an accurate thermography conversion function over this narrow range of interest. However, in practice, given the narrow temperature range needed, the arrangement shown in FIG. 1 has been shown to achieve acceptable results.

In Step 530, using pattern recognition of the visible image, pixels and thermal pixels representing a region of interest on the target are identified, and the thermal pixel region to be used may be refined from information from both the thermal and visible images. The region of interest may correspond, for example, to the facial region 145 of interest in the face 135 of a target 130, as shown in FIG. 2. In step 540, the specific refined region pixels corresponding to the region of interest are known on the thermal image and the thermography function has been recently updated at the temperature of interest for these pixels to produce a real time calibrated temperature measurement of this region. Thus, at the conclusion of the method of FIG. 5, the temperature in a narrow range about the temperature of interest is derived with high accuracy for the region of interest pixels, even for a low-performance thermal imager.

Figure 6:
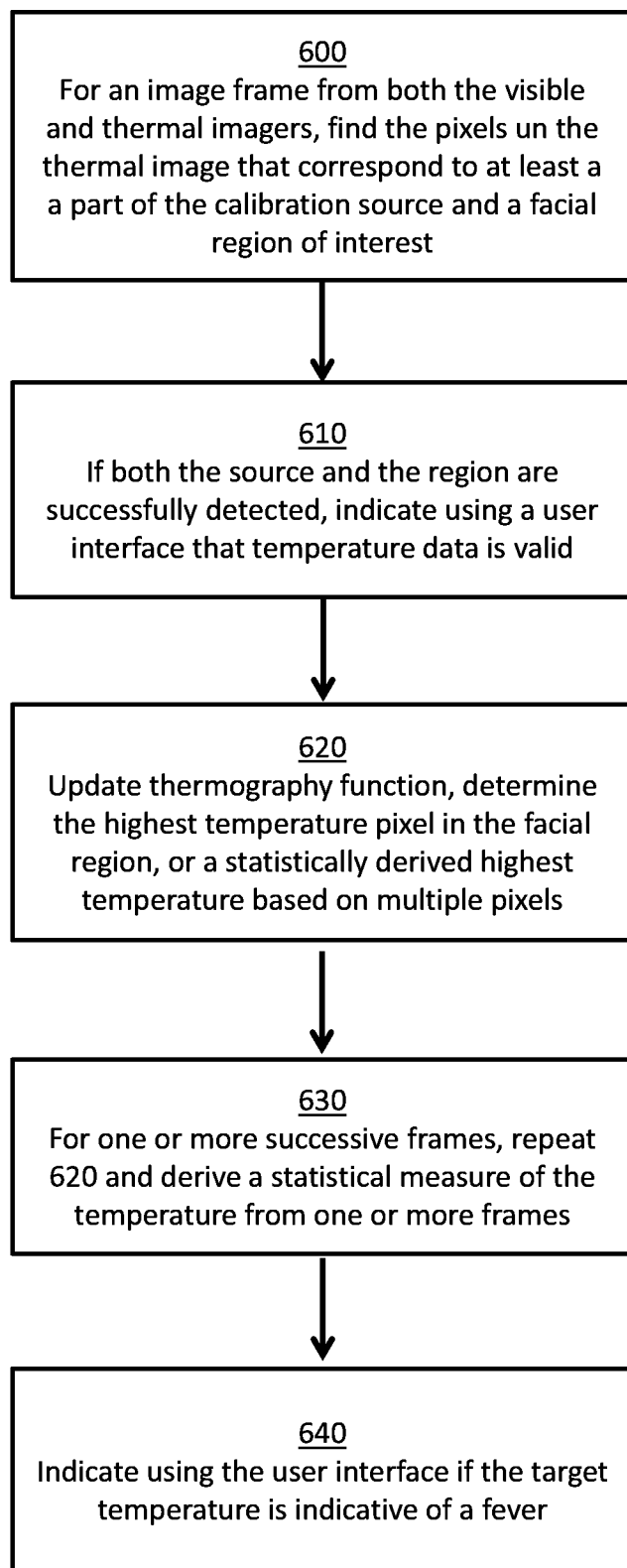
FIG. 6 is a flow chart illustrating an exemplary method of operation of a thermal imaging system for a fever detection application in accordance with the present technology.

Referring to FIG. 6 a process for using the system of FIG. 1 specifically tailored to the fever detection is shown. FIG. 6 may be similar to an implementation of the process of FIG. 5 in which the target is a human being and the temperature of interest is a temperature indicative of a fever. This process assumes that the various steps are performed on a frame by frame basis of the thermal camera (frame rates for the visible camera are usually higher, so frame rates in this discussion refers to thermal frame rate). Any and all of these steps could be performed at other time periods rather than per frame. It is understood that as long as the steps are generally close in time (e.g., within about 5 seconds, 10 seconds, 15 seconds, etc.) the specific times are not critical. However, performing on a frame-by-frame basis based on image frames obtained by the thermal imager is possible for this application and may simplify the process logic.

In step 600, using pattern recognition/facial recognition, the system finds the thermal pixels in a thermal image frame corresponding to a facial region of interest on a human target and thermal pixels corresponding to the thermal calibration source. In some embodiments, the calibration source may be at or near human body temperature, and the facial region may correspond to the areas around the eyes and the bridge of the nose.

In some embodiments, it may be useful to let users know if both the face and the source are detectable. Therefore, as shown in optional step 610, the system may, through a user interface, indicate that data is valid or invalid. For example the system may provide an indication that the data will not be valid if the target, region of interest, and/or calibration source are not visible and/or cannot be detected using the implemented facial recognition and/or pattern recognition algorithms. The indication may be audio or visible, and may include an indicator light and/or a notification provided via an interfaced computing device.

In step 620, the system can update the thermography function of the thermal camera, based on the known temperature of the calibration source, and can use the updated thermography function to determine the temperature of pixels in the facial region of interest. Various methods of determining a temperature of pixels in the facial region of interest are possible. In one example, the highest-temperature pixel in the region is recorded for each frame. In another example, some number of the highest-temperature pixels (e.g., the top 5 hottest pixels, the top 10 hottest pixels, the top 20 hottest pixels, etc.) can be recorded. Other statistically derived temperatures are possible, for example, the average or median of a predetermined number of pixels (e.g., the top 5 hottest pixels, the top 10 hottest pixels, the top 20 hottest pixels, etc.) or of all pixels within the facial region of interest, or any of a variety of approaches. Regardless of the specific method chose, step 620 results in a temperature value or a plurality of temperature values being derived for the region of interest in a particular frame.

In step 640, single-frame temperatures may be combined with other frames (e.g., values determined using the process of step 620) statistically to yield a more reliable temperature result. In one example, the highest-temperature pixel from each frame is boxcar averaged with that from some number of successive frames, 8 for instance. Since a common frame rate for low-cost thermal imagers is 8 Hz, only one second is required to acquire the 8 frames of thermal image data for this example method. Other statistical derivations based on the data from multiple frames are possible.

The temperature result may be indicated on a user interface in a variety of audio or visible ways, or even reported across a network or to a computing device if the unit is so interfaced. In some embodiments, a simple indicator light color may be used to indicate a target may have a fever. Fever indication may be by way of determining that the actual temperature is above a threshold relative to a target temperature, the target temperature in the simplest case being a nominal value corresponding to expected or known normal body temperature. It is also possible to take or store a visible wavelength picture of targets, say those suspected of having a fever, as well.

Figure 7:
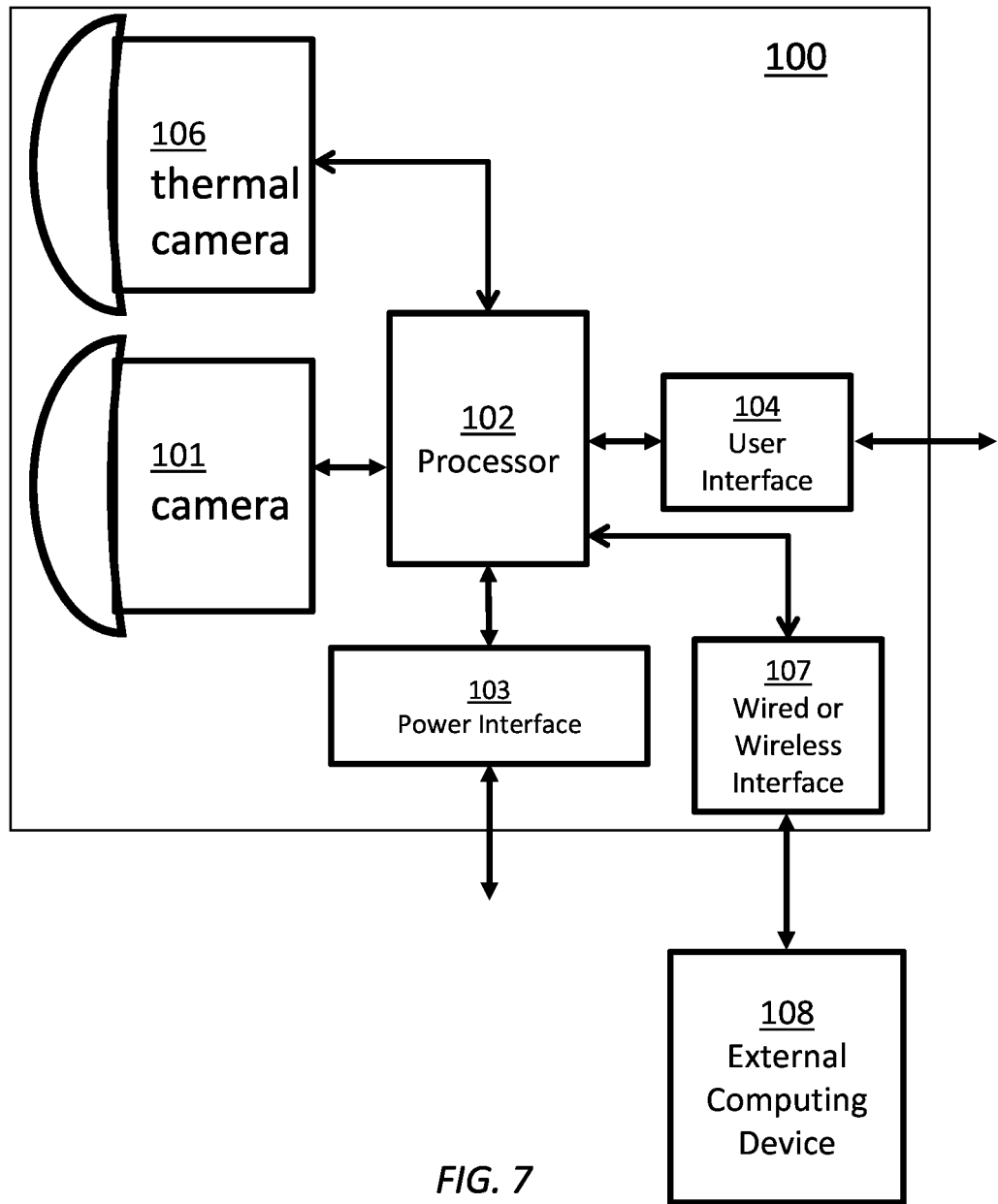
FIG. 7 is a schematic representation of an exemplary imager interfaced to an external computing device in accordance with the present technology.

FIG. 7 schematically illustrates an alternative version of an imaging unit 100, where the operation and user interaction is a combination of monitored or controlled by an external computing device 108. In this case, a wired or wireless interface 107 connects the control processor 102 to the external device 108. In this configuration, the fever detection may be less automated. For instance, a user could be monitoring the visible and/or thermal camera views on a display of the external computing device 108 and may either enable data capture or disable depending on what is observed on the display. Data logging may also be supported. For instance, temperature data and a visible and/or thermal image could be logged for each target, and correlated and/or later displayed in a variety of ways. Temperature trends and patterns over periods of time and/or number of targets could be analyzed. In another example, a user may directly monitor temperatures as targets pass through the thermal imaging system and initiate action in response to what is viewed on the display as well as or in place of a simplified user interface as described above.

Figure 8:
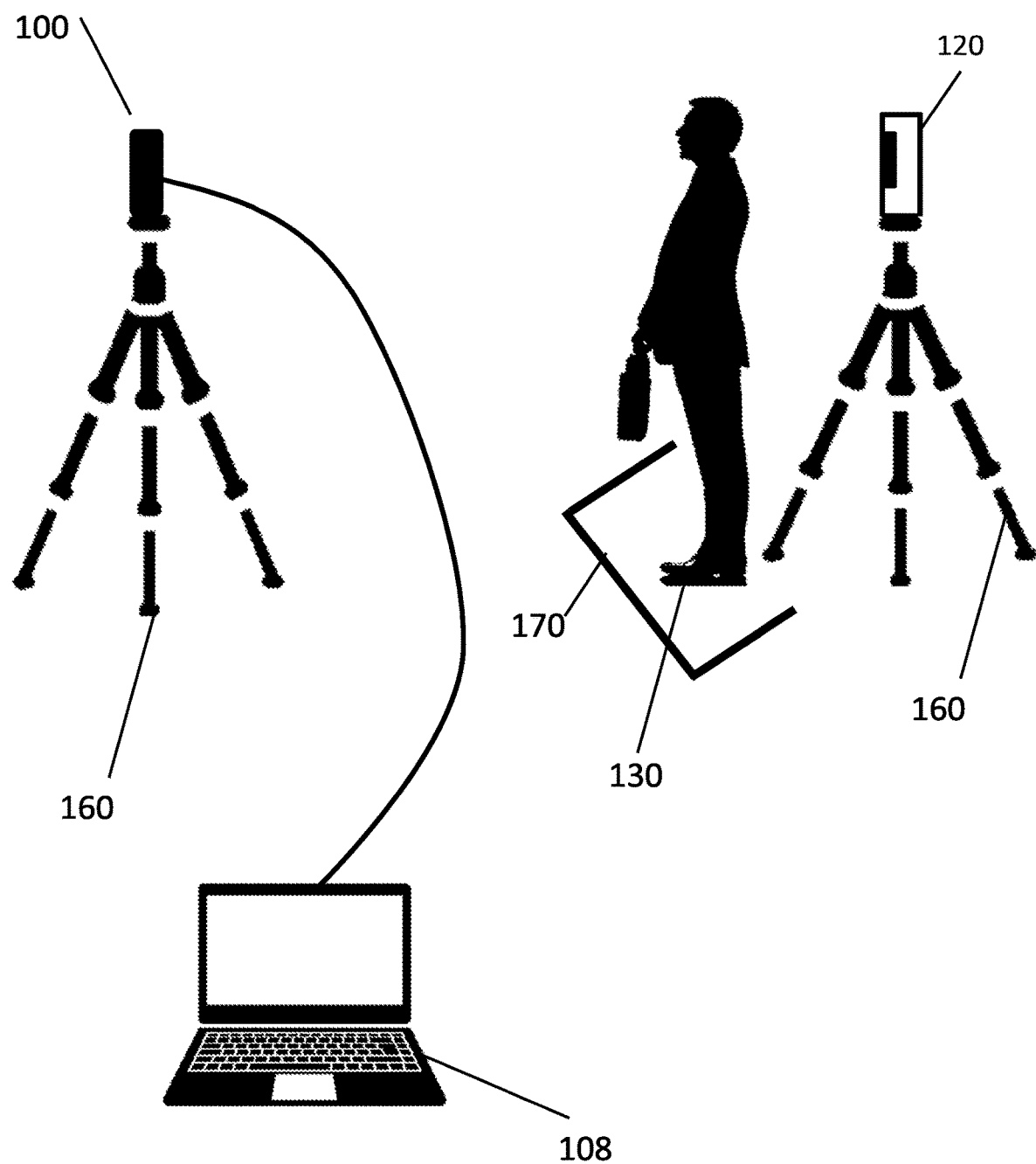
FIG. 8 schematically illustrates an exemplary arrangement of a thermal imaging system in use in accordance with the present technology.

FIG. 8 shows a further arrangement of a thermal imaging system in accordance with the present technology. In some implementations, the system of FIG. 8 can be replicated in any desired location, including locations where a constrained space (e.g., space 110 of FIG. 1) does not exist. Rather than rely on a constrained target scenario, the imaging unit 100 and thermal calibration source 120 may be conveniently placed where desired. For instance, the imaging unit 100 and thermal calibration source 120 may be placed on tripods 160 or other physical support structures as shown at known separations and alignments, and the targets 130 may be directed by markings 170 (e.g., temporary or permanent markings such as tape, paint, chalk, or the like) on the floor. For cases where an external computing device 108 is present, the external computing device 108 may be placed as needed. Thus as shown, the system may be portable and may be quickly installed and operable in just about any conceivable environment, allowing for great flexibility in use and application. Other mounting arrangements are possible, including purpose-built mounts, or any existing suitable mounting systems other than tripods. Mounting systems may be permanent or temporary, and may in any combination attach to floors, walls, or ceilings as appropriate for a particular setting.

Figure 9:
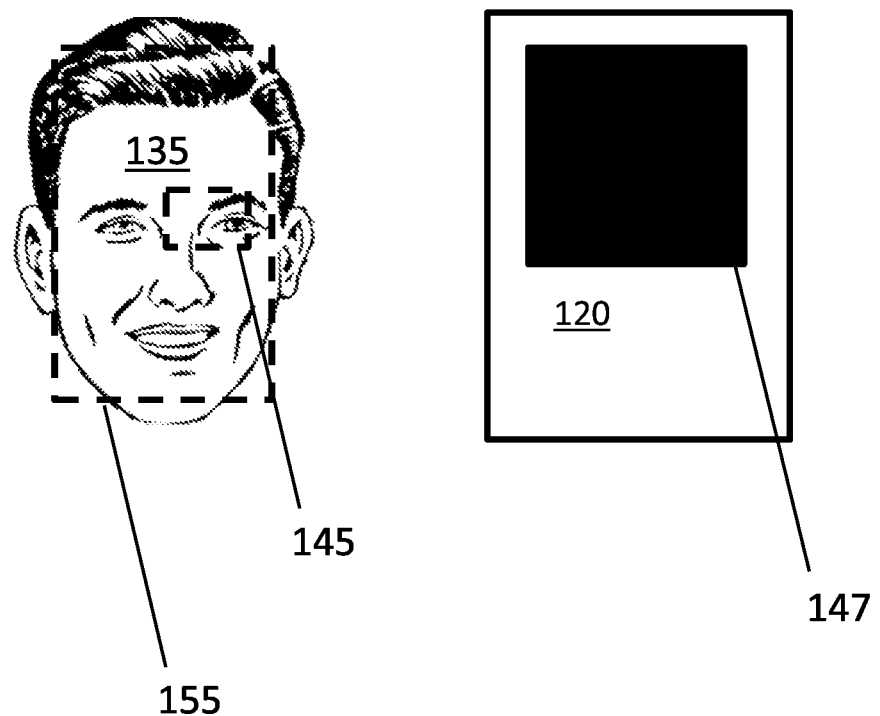
FIG. 9 shows details of an exemplary thermal imaging system relative to recognition of regions of interest and areas that can be used for distance estimates.

Various arrangements of facial recognition are possible. In general, it appears that a simple facial recognition of the region of interest in the visible image and then mapping that recognized region to the corresponding thermal pixels should be adequate. This is often not the case and in fact pattern recognition on both images, or repeated steps in either/or image may generate information useful to refine the thermal pixel region of interest. Some examples are described below. For instance, as shown in FIG. 9, a two-step facial recognition process may be implemented. In an example two-step facial recognition process, a face 135 of a target may first be detected using known facial recognition technologies. Based on the detected face 135, a facial region 155 of pixels corresponding to a relatively large region including most or all of the face may be determined. Further facial recognition and/or pattern recognition algorithms may be implemented on the pixels of the facial region 155 to detect a more specific region of interest 145 which may then be used for temperature detection as described elsewhere herein. Many varieties of facial and pattern recognition may be employed.

Figure 10:
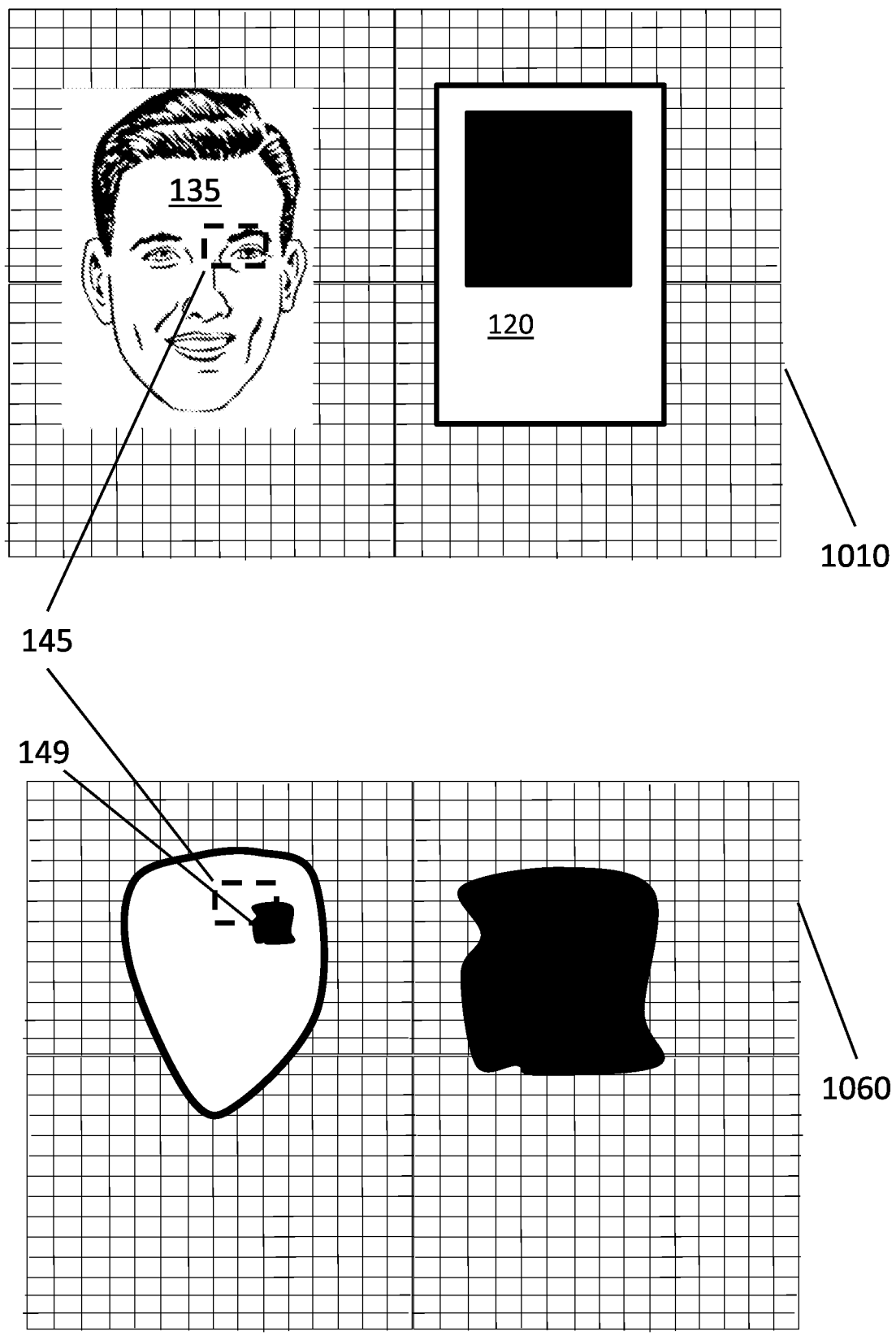
FIG. 10 shows elements recognized for a facial recognition approach using a combination of thermal and visible image data.

As previously stated, the facial region identified from the visible image is often sufficient. There are sources of error, such as misalignments in the thermal and visible imager that affect the mapping accuracy between the two images depending on distance and aiming and other effects. It may be useful, as shown in FIG. 10, to improve the facial region recognition using thermal as well as visible data. The mapped thermal facial region determined from the visible facial recognition area, shown as 149 in FIG. 10, may be further inspected for pixels within a predetermined temperature range of the source temperature that are within/o a predetermined distance, radius, or more likely x,y coordinates, of the mapped pixels. These pixels in an ideal situation would align with the pixels derived from the visible to thermal mapping. As shown in the figure, there may in fact be an offset between the two regions. A statistical measure of the two regions' relative centers, relative boundary positions, or the like, may be determined and the offset between the regions may be determined. As the offset may change, depending on target distance and orientation, it may be useful to make this offset correction dynamically, even frame by frame. For example, the offset in x,y coordinates may be determined between the positions (weighted centers, side positions, or other suitable measures) and determined on a frame by frame basis. Any statistical or even single point utilization of the offsets may be useful. For example, on a frame by frame basis, a distribution chart (e.g., binning) of each observed x and y offset may be created; the bins with the highest count may be used for real-time x and y offset of the thermal facial region for that frame. Other statistical or direct ways to use the offsets derived may be suitable as well. This is an example of refining the target thermal pixel region with information beyond what is available from the visible facial recognition.

Other refinements may be beneficial as well. It is also possible that facial recognition using the visible image may fail for some targets and/or under some conditions. In this case it may be possible to recover and still make an acceptable temperature measurement using primarily or only thermal data to recognize a suitable facial region. Since the calibration source temperature is chosen to be near the expected range of body temperatures, the thermal data can be analyzed and regions identified where a number of pixels within a region of the imaged thermal scene fall within a range of the calibration source temperature. For example, the thermal image may be parsed into appropriately sized regions, where the size may be determined empirically, or chosen to correspond to an expected or historically derived region size from visible images with successful facial recognition. So this process may identify one or more appropriately sized regions where a predetermined proportion, number, or percentage of the pixels in that region meet temperature criteria. Once these regions are identified, they may be refined by narrowing the temperature range to a range closer to the expected body temperature (e.g., down to as little as 2-3 degrees) until a candidate region is identified where a given proportion of the pixels lies within a predetermined smaller desirable range. This region may be used for the temperature determinations as described above.

This process may be done in parallel with the visible facial recognition process, as it can be done with computationally efficient image processing techniques, and the facial recognition may switch over to the thermal if the visible fails after a certain number of tries. In one non-limiting example embodiment, on each frame, the thermal image is first parsed into one or more appropriately sized regions where a predetermined proportion of the pixels in the regions are within, for example, 8 degrees of the calibration source temperature. Then the temperature discrimination range can be lowered to tighter thresholds around the expected body temperature range, possibly incrementally or in one or two range decreases, until a region is identified with a sufficient number of pixels within the smallest range that still leaves at least one region meeting the size and temperature criteria. In this embodiment, if visible facial recognition fails for a predetermined number of successive frames, such as 8 successive frames, the region determined in parallel during those 8 frames as described is used in place of a visibly determined facial region.

As discussed above, errors may be introduced over time in thermography functions for thermal imaging, which may be addressed by the calibration methods and devices disclosed herein. However, another source of error in thermography functions for thermal imaging is that the intensity signal corresponding to a given scene temperature may vary based on the scene distance from the imager. Thus, a typical calibrated thermography function provides an accurate scene temperature at a fixed difference relative to the imager, while the temperatures of scenes at other distances may be incorrect. As has been shown above, the body temperature system may be set up in a variety of environments, and within a given environment, the location of the target (including the distance between the target and the imager) may vary to some degree, often for every temperature measurement cycle. However, the actual image size of the active area 121 of the calibration source 120 (e.g., a dimension in image frame pixels) can be known at a nominal distance from source to imager. Therefore, based on the known nominal size within an image frame of the active area 121, the actual image size can be compared to nominal distance size, and an accurate measure of actual distance from source to imager can be known. The mathematics to adjust thermography functions for scene distance is known.

Compensation for variation in distance may be a bit more complicated for the target facial region 145, as target size varies. However, in practice for a facial region 145 constrained to the region around an eye, as shown, the variation, even from adults to children, is surprisingly small. Thus, the nominal distance size 145 can be compared to the actual region size and an estimate of actual distance that significantly reduces the distance thermography error can be derived.

Figure 11A:
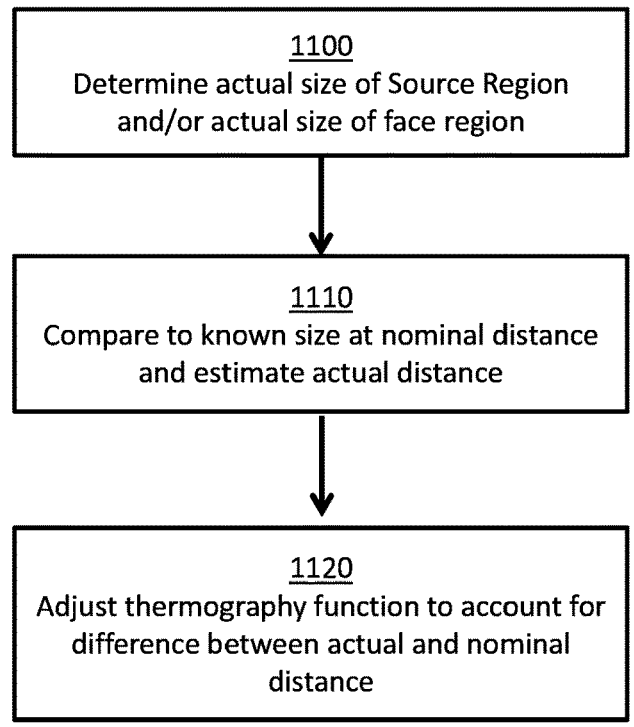
FIG. 11A is a flow chart illustrating an exemplary distance correction method in accordance with the present technology.

FIG. 11A is a flow chart illustrating an example distance correction process as described herein. In step 1100, the actual size of the source and/or facial region at the actual imager distances to the source and the target are determined. In step 1110, the actual size is compared to the known size at nominal distances, which may be predetermined and stored in a memory of the imaging unit 100. An estimate of distance to both target and source may then be made based on the comparison to known size at nominal distance. In step 1120 the thermography function is adjusted for the estimated differences to improve the accuracy of the temperature measurements.

Figure 11B:
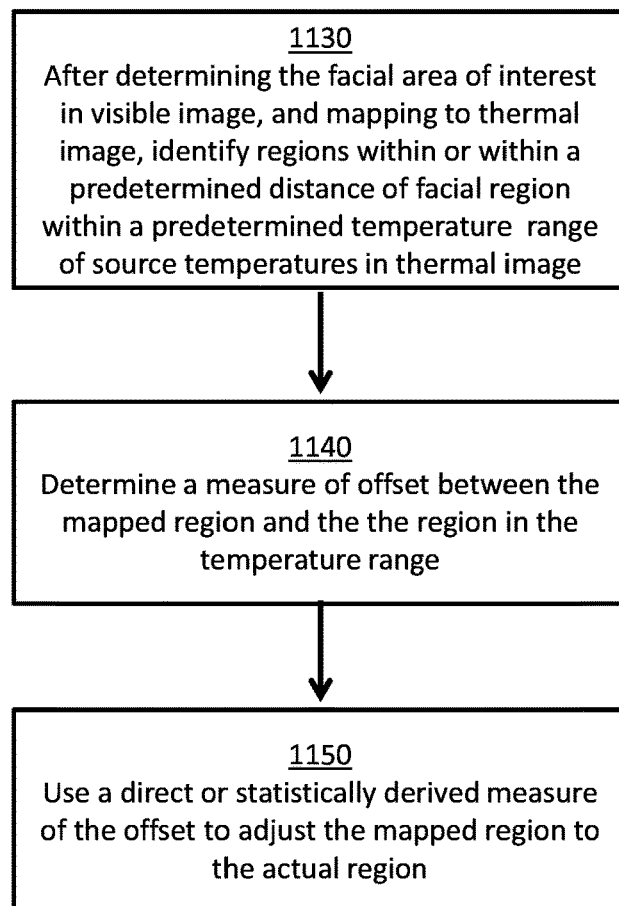
FIG. 11B is a flow chart illustrating an exemplary dual facial recognition method in accordance with the present technology.

FIG. 11B is a flow chart illustrating an example facial recognition modification based on thermal data. In step 1130, after the visible face recognition has been accomplished and the corresponding mapped thermal pixels are identified, pixels within or within a range of the mapped thermal region are identified that are within a predetermined temperature range of the source temperature. In step 1140, the offset between the expected facial region and the region determined in step 1130 is determined. In step 1150, either a direct or statistically derived offset is used to adjust the position of the thermal facial region.

For some situations, the ambient environment may have a significant effect on external body temperature, which can in turn introduce errors in setting a threshold above which fever is suspected. For instance, if monitoring is performed on people who have been waiting in a line outdoors, and the measurement is performed just inside an entrance, it is possible that skin temperatures may be higher or lower than expected nominal values. Also, body temperature varies naturally over the course of a day, and ambient temperature, particularly outdoors, also varies over time. Thus, using a nominal target temperature to set a threshold for fever indication may in practice not provide good results as the actual body temperature may vary too much, possibly even as much as several degrees which may be larger than the threshold range over nominal target temperature.

Accordingly, for some situations, rather than use a fixed target body temperature, results may improve if the target temperature is determined adaptively during use. An example adaptive approach is described below.

Figure 12:
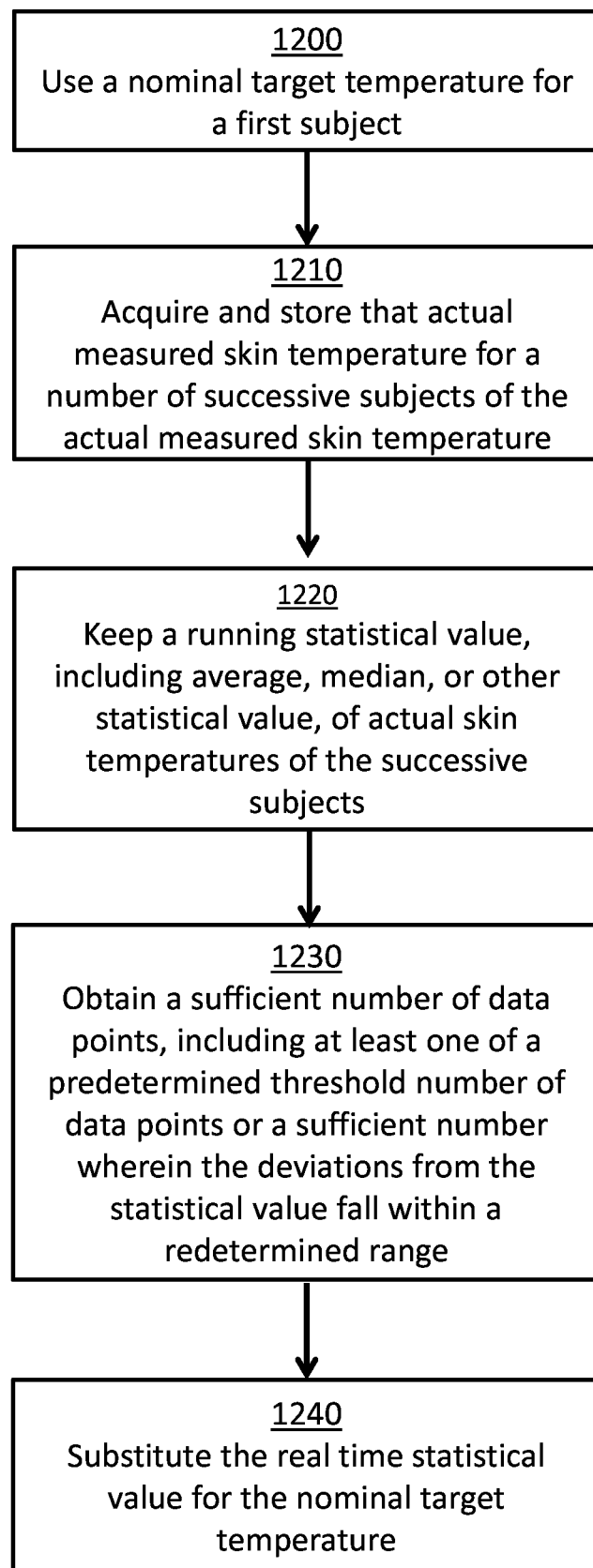
FIG. 12 is a flow chart illustrating an exemplary adaptive threshold temperature determination method.

In one particular non-limiting example adaptive approach, shown in FIG. 12, in step 1200 for the first subject tested, a nominal target temperature is used, but, in step 1210, for successive subjects the actual measured skin temperature is kept, and, in 1220, a running statistical value (average, median, or other statistical value) of actual skin temperature is determined. In step 1230, after a sufficient number of data points are obtained (e.g., a predetermined threshold number of data points or until the deviations from the running statistical values are within an acceptable range), and in step 1240, the real time statistical value is substituted for the nominal target temperature.

In one example, after 15 subjects have been measured, outliers may be eliminated, say the three highest and lowest values, and the center values (e.g., the remaining values after the outliers are eliminated) averaged. The average of the center values can then be used as the target temperature and the threshold for fever indication is applied to the adaptive average. Then the running adaptive target may be updated continuously after the first fifteen subjects (e.g., after every subsequent subject, or periodically such as after every 2, 3, 4, 5, 10, or more subjects). The cycle may be restarted at any time and newly finding the adaptive target.

Variations, such as number of subjects used, how many subjects are tested before the adaptive statistical value is used, number of outliers removed if any, how the adaptive data is mixed into the target number (e.g., whether the adaptive statistical value is directly substituted for the nominal target temperature or is brought in fractionally such as by a weighted average or other combination with the nominal target temperature), and which statistical measure is applied are all possible, as well as other variations that may occur. Preferably, the target temperature is based on real time or near-real time actual subject data, which has the effect of smoothing out the cyclical variations in body temperature due to ambient and time of day effects.

Depending on the embodiment, certain acts, events, or functions of any of the processes described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and process steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. For example, the LUT described herein may be implemented using a discrete memory chip, a portion of memory in a microprocessor, flash, EPROM, or other types of memory.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, and Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices or processes illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system for measuring the temperature of a region of interest of a target, the system comprising:
    at least one system controller;
    at least one visible camera interfaced to the controller;
    at least one thermal camera interfaced to the controller, wherein at least a portion of image pixel locations from the visible and thermal cameras are mapped to each other, and wherein the thermal camera has a thermography function based on a previous pixel-by-pixel calibration of at least some pixels of the thermal camera; and
    at least one temperature controlled calibration source of a known shape;
    wherein, when the target and the calibration source are within a field of view (FOV) of both cameras, the system controller is configured to:
        obtain a visible image using the at least one visible camera and a thermal image using the at least one thermal camera;
        locate the calibration source in the thermal image by performing pattern recognition on at least one of the visible image and the thermal image;
        perform a temperature calibration of a subset of pixels in the thermal image, the subset of pixels corresponding to the calibration source;
        update a thermography function of the thermal camera based on a known temperature of the calibration source, the known temperature of the calibration source being at least one of within 15 degrees, within 10 degrees, or within 5 degrees of a nominal human body temperature;
        detect, using pattern recognition, visible region of interest pixels in the visible image and thermal region of interest pixels in the thermal image;
        refine the thermal region of interest pixels based on the pattern recognition;
        perform an updated thermography readout of the refined thermal region of interest pixels to produce a real-time calibrated temperature measurement based on the thermal region of interest pixels, the temperature measurement being within a range corresponding to within at least one of 15 degrees, 10 degrees, or 5 degrees above the nominal human body temperature; and periodically update detection and mapping of the visible region of interest pixels, update location of the calibration source, and update the temperature calibration after a number of frames, wherein the number of frames is one and the periodically updating is performed on a frame-by-frame basis.

2. The system of claim 1, wherein the target comprises an upper body region of a human, and wherein the region of interest comprises a portion of a facial region of the target.

3. The system of claim 1, wherein the temperature measurement is a threshold measurement indicative of the target having a fever.

4. The system of claim 1, wherein the threshold temperature measurement is based on a highest temperature pixel of the thermal region of interest pixels, statistically derived over the number of frames.

5. The system of claim 4, wherein the number of frames is 8 and the statistical derivation is a boxcar average of the highest temperature pixel of the thermal region of interest pixels in each of the 8 frames.

6. The system of claim 5, wherein the threshold temperature measurement is based on a statistical derivation of a number of the highest temperature pixels in the region and is derived over one or more frames.

7. The system of claim 1, further comprising a user interface interfaced to the system controller, the user interface comprising at least one of audio or visible indicators indicating at least one of measurement validity based on verified detection of the target and the calibration source or a target temperature above a threshold.

8. The system of claim 1, wherein locating the calibration source in the thermal image comprises at least one of identifying pixels of the known shape of the calibration source in the thermal image, or recognizing at least one of the source shape or color in the visible image and mapping to the corresponding thermal pixels.

9. The system of claim 1, wherein pixels in a mapped facial region within a predetermined temperature range of the calibration source temperature are identified, and facial region coordinates in the thermal image are updated based on the identified pixels.

10. The system of claim 1, wherein an actual size of at least one of the calibration source and a facial region are compared to the known size at a nominal distance from the cameras, and wherein the thermography function is adjusted for distance based on an estimated distance between the at least one thermal camera and the at least one of the calibration source and the facial region, the estimated distance being determined based on the comparison.

11. The system of claim 1, wherein the system controller is further configured to:
use a nominal target temperature for a first target;
acquire and store actual measured skin temperatures for a number of successive targets;
keep a running statistical value, including at least one of an average, median, or other statistical value, of actual skin temperatures of the successive targets;
obtain a number of data points including at least one of a predetermined threshold number of data points or a number of data points such that deviations from the statistical value fall within a predetermined range; and
substitute the running statistical value for the nominal target temperature for at least some subsequent temperature measurements.

12. The system of claim 11, wherein outliers are eliminated, and a statistical value of remaining center temperatures are used as the nominal target temperature.

13. The system of claim 11, wherein the nominal target temperature is periodically updated after at least one of every successive target after the initial number or after a predetermined number of targets.

14. A method for measuring the temperature of a region of interest of a target with a system comprising at least one visible camera and at least one thermal camera interfaced to a system controller, wherein at least a portion of image pixel locations from the visible and thermal cameras are mapped to each other, and wherein the thermal camera has a thermography function based on a previous pixel-by-pixel calibration of at least some pixels of the thermal camera, the system further comprising at least one temperature controlled calibration source of a known shape, the method comprising:
causing the target and the calibration source to be within a field of view (FOV) of both cameras;
obtaining a visible image using the at least one visible camera and a thermal image using the at least one thermal camera;
locating the calibration source in the thermal image by performing pattern recognition on at least one of the visible image and the thermal image;
performing a temperature calibration of a subset of pixels in the thermal image, the subset of pixels corresponding to the calibration source;
updating a thermography function of the thermal camera based on a known temperature of the calibration source, the known temperature of the calibration source being at least one of within 15 degrees, within 10 degrees, or within 5 degrees of a nominal human body temperature;
detecting, using pattern recognition, visible region of interest pixels in the visible image and thermal region of interest pixels in the thermal image;
refining the thermal region of interest pixels based on the pattern recognition;
performing an updated thermography readout of the refined thermal region of interest pixels to produce a real-time calibrated temperature measurement based on the thermal region of interest pixels, the temperature measurement being within a range corresponding to within at least one of 15 degrees, 10 degrees, or 5 degrees above the nominal human body temperature; and
periodically updating detection and mapping of the visible region of interest pixels, updating location of the calibration source, and updating the temperature calibration after a number of frames, wherein the number of frames is one and the periodically updating is performed on a frame-by-frame basis.

15. The method of claim 14, wherein the target comprises an upper body region of a human, and wherein the region of interest comprises a portion of a facial region of the target.

16. The method of claim 14 wherein the temperature measurement is a threshold measurement indicative of the target having a fever.

17. The method of claim 14, wherein the threshold temperature measurement is based on a highest temperature pixel of the thermal region of interest pixels, statistically derived over the number of frames.

18. The method of claim 17, wherein the number of frames is 8 and the statistical derivation is a boxcar average of the highest temperature pixel of the thermal region of interest pixels in each of the 8 frames.

19. The method of claim 18, wherein the threshold temperature measurement is based on a statistical derivation of a number of the highest temperature pixels in the region and is derived over one or more frames.

20. The method of claim 14, wherein the system includes a user interface interfaced to the system controller, the user interface comprising at least one of audio or visible indicators indicating at least one of measurement validity based on verified detection of the target and the calibration source or a target temperature above a threshold.

21. The method of claim 14, wherein the source location is further derived by recognizing at least one of the source shape or color in the visible image and supplementing the data from the thermal image.

22. The method of claim 16 wherein the pixels in the mapped facial region within a predetermined temperature range of the source temperature are identified, and the facial region coordinates in the thermal image are updated based on the temperature identified pixels.

23. The method of claim 14, wherein an actual size of at least one of the calibration source and a facial region are compared to a known size at a nominal distance from the cameras, and wherein the thermography function is adjusted for distance based on an estimated distance between the at least one thermal camera and the at least one of the calibration source and the facial region, the estimated distance being determined based on the comparison.

24. The method of claim 14, further comprising:
using a nominal target temperature for a first target;
acquiring and storing actual measured skin temperatures for a number of successive targets;
keeping a running statistical value, including at least one of an average, median, or other statistical value, of actual skin temperatures of the successive targets;
obtaining a number of data points including at least one of a predetermined threshold number of data points or a number of data points such that deviations from the statistical value fall within a predetermined range; and
substituting the running statistical value for the nominal target temperature for at least some subsequent temperature measurements.

25. The method of claim 24, wherein outliers are eliminated, and a statistical value of remaining center temperatures are used as the nominal target temperature.

26. The method of claim 24, wherein the nominal target temperature is periodically updated after at least one of every successive target after the initial number or after a predetermined number of targets.

* * * * *